(12) United States Patent
Szeles

(10) Patent No.: US 7,660,637 B2
(45) Date of Patent: Feb. 9, 2010

(54) ELECTRODE SYSTEM FOR ELECTRIC POINT STIMULATION THERAPY AND A MANIPULATION TOOL THEREFOR

(75) Inventor: Josef Constantin Szeles, Glanzinggasse 5/7, Vienna (AT) A-1190

(73) Assignee: Josef Constantin Szeles, Vienna (AU)

( * ) Notice: Subject to any disclaimer, the term of this patent is extended or adjusted under 35 U.S.C. 154(b) by 370 days.

(21) Appl. No.: 10/432,336

(22) PCT Filed: Nov. 16, 2001

(86) PCT No.: PCT/AT01/00362

§ 371 (c)(1),
(2), (4) Date: May 20, 2003

(87) PCT Pub. No.: WO02/41943

PCT Pub. Date: May 30, 2002

(65) Prior Publication Data

US 2004/0044390 A1 Mar. 4, 2004

(30) Foreign Application Priority Data

Nov. 21, 2000 (AT) .............................. GM859/2000

(51) Int. Cl.
*A61N 1/04* (2006.01)
(52) U.S. Cl. ..................................................... 607/150
(58) Field of Classification Search ................. 607/142, 607/115; 600/372
See application file for complete search history.

(56) References Cited

U.S. PATENT DOCUMENTS

| | | | |
|---|---|---|---|
| 3,939,841 A | | 2/1976 | Dohring et al. |
| 4,685,466 A | * | 8/1987 | Rau ........................... 600/387 |
| 5,449,378 A | * | 9/1995 | Schouenborg ............... 607/46 |
| 5,772,688 A | * | 6/1998 | Muroki .......................... 607/1 |
| 5,957,862 A | | 9/1999 | Lu et al. |
| 6,493,592 B1 | * | 12/2002 | Leonard et al. ............. 607/149 |
| 6,539,264 B1 | * | 3/2003 | Bishay et al. ................. 607/46 |

FOREIGN PATENT DOCUMENTS

| | | |
|---|---|---|
| AT | 395 106 | 9/1992 |
| EP | 0 759 307 | 2/1997 |
| GB | 2 115 700 | 9/1983 |

* cited by examiner

*Primary Examiner*—George R Evanisko
*Assistant Examiner*—Alyssa M Alter
(74) *Attorney, Agent, or Firm*—Collard & Roe, P.C.

(57) ABSTRACT

An electrode system (1) for an electric punctual stimulation therapy, which system comprises at least one stimulation electrode (4) with a disk-like base (5) and has an annular platelet (9) to be arranged on the skin surface (2) before the latter is pierced by the electric needle (7), which annular disk (9) is glued to the skin surface (2) and is connected to the base (5) via an adhesive connection, and a handling tool (21) for applying such an electrode system. The handling tool (21) comprises an electrically conductive, axially displaceable pin (25) which is connected to a resistance measurement device (40) and which is also designed to put the annular platelet (9) thereon and apply it. Preferably, the electrode can also be fitted to the tool (21).

16 Claims, 4 Drawing Sheets

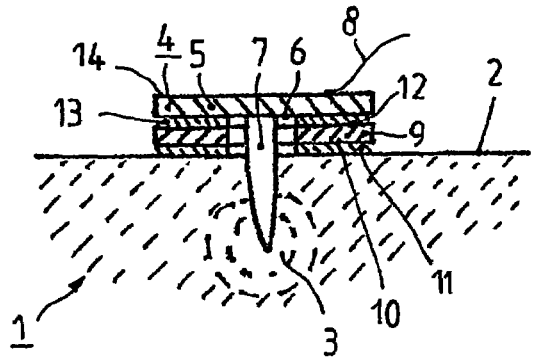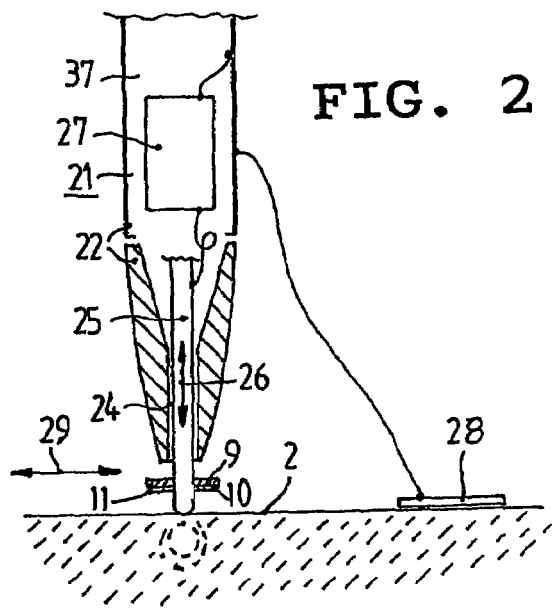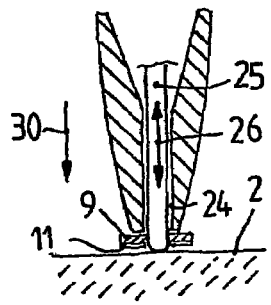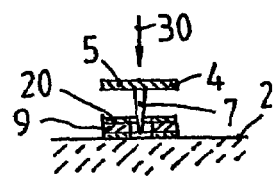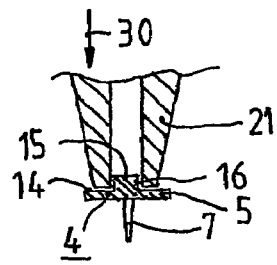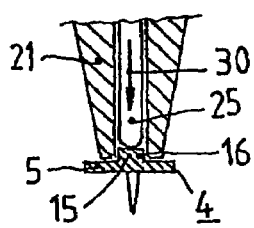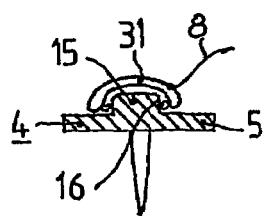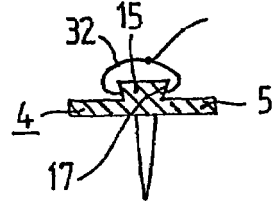

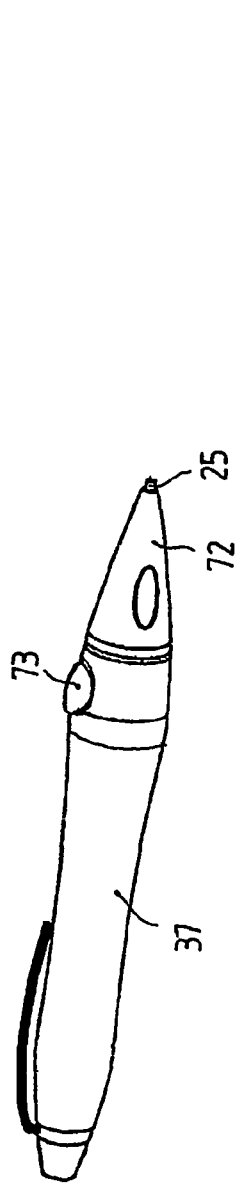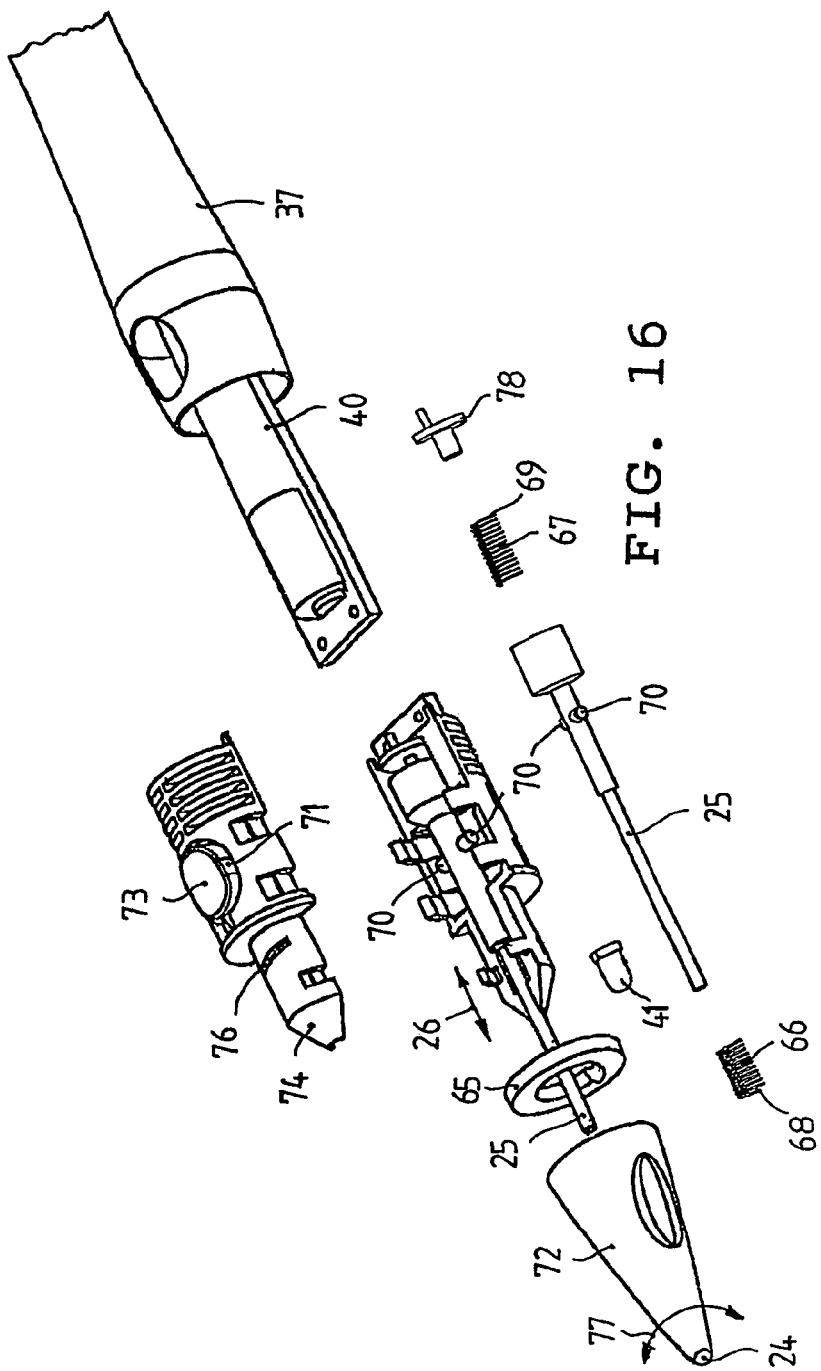

ELECTRODE SYSTEM FOR ELECTRIC POINT STIMULATION THERAPY AND A MANIPULATION TOOL THEREFOR

The invention relates to an electrode system for an electric punctual stimulation therapy, comprising at least one punctual stimulation electrode to be arranged at receptor regions located below the skin surface, which punctual stimulation electrode comprises a disk-like base which, in the middle thereof, at its side that is to face the skin surface, is provided with a needle or tip via which an introduction of current into the receptor region to be stimulated occurs, this punctual stimulation electrode being fed from a treatment current generator via a flexible line. Furthermore, the invention relates to a handling tool for applying such an electrode system to the skin surface.

The electric punctual stimulation therapy, which also includes various forms of electric acupuncture, can successfully be employed for various health disturbances, such as, e.g., allergies, asthma, adipositas, pain. Often a treatment that lasts for several hours or even for several days is considered suitable in this case. In this instance, also the mobility of the patient to be treated is to be restricted as little as possible, and, if possible, the treatment should be practicable while living a largely normal life, including working on a paid job. Accordingly, the attachment and design of electrodes used in such a punctual stimulation therapy is very important. For a highly effective stimulation of the receptor regions relevant in the respective case of treatment, an exact positioning of the electrodes in these regions is particularly important. A secure fit of the electrodes at the receptor regions to be stimulated over extended periods of time is to be ensured even if slighter mechanical forces act unintentionally on the electrodes during treatment.

With known electrodes of the initially mentioned type (AT 395106B), in the center of the disk-shaped base, a needle is provided at its side to face the skin surface, which needle is provided with a sharp-edged thread. In addition, also on the side of the electrode which is to face the skin surface, an adhesive glue may be provided. Considering the smallness of the dimensions commonly found in the needle, the thread provided on the needle causes often undesired additional production expenditures and also requires a sensitive targeting and turning of the electrode when piercing a receptor region to be stimulated, the presence of an adhesive glue at the disk-like base towards the end of the insertion procedure or piercing procedure with such an electrode possibly also resulting in an undesired competing action between the rotating movement to be carried out when piercing with the needle of the electrode and an already starting adhesion of the adhesive glue at the skin surface.

It is an object of the present invention to provide an electrode system of the initially defined type which allows for a very simple manipulation when applying it to a receptor region to be stimulated, wherein also the localizing of a suitable receptor region and as exact a positioning as possible of the stimulating electrode at the localized receptor region is to be feasible in a simple manner and, moreover, also a stable hold of positioned electrodes is to be ensured.

The inventive electrode system of the initially mentioned type is characterized in that for fixing the respective punctual stimulation electrode at the skin surface, an annular platelet is provided which is to be arranged on the skin surface prior to an application of the electrode thereto or piercing thereof, which annular platelet has an adhesive layer at its side to face the skin surface for an adhesion to the skin surface and that, furthermore, an adhesive connection is provided between the other side of this annular platelet and the side of the base of the punctual stimulation electrode that comprises the needle or tip. By this design of the electrode system, the previously mentioned object can well be met. By the fact that the annular platelet is separately arranged at the skin surface before an application of the electrode thereto or piercing thereof, this annular platelet can be placed and closely pressed to the skin surface without taking into consideration any requirements which arise during a piercing with the electrode, so that a good adhesive action can be achieved in a simple manner. Moreover, also by the aperture present in the annular platelet, a highly exact positioning of this annular platelet at the receptor region to be stimulated is provided, it being particularly possible to pass a tracing pin or a tracing electrode through the aperture present in the annular platelet and to determine the position of receptor regions when moving the tracing pin or the tracing electrode, respectively, over the skin surface, it being possible to precisely press the annular platelet to the skin surface when a receptor region has been reached. The receptor region intended to be stimulated is clearly marked by the annular platelet glued to the skin surface, and thus the punctual stimulation electrode to be arranged can very easily and precisely be positioned when being arranged at this receptor region or piercing the same, and moreover, by the annular platelet, a clearly defined support is created at which the disk-like base of the punctual stimulation electrode comes to lie when applying this electrode or piercing the skin surface therewith, and will be securely fixed by means of an adhesive connection without irregularities of the skin surface having an adverse effect. As the adhesive connection, preferably a glued connection is provided which may, e.g., be realized in that an adhesive layer is also provided at the surface of the annular platelet that faces away from the skin surface. In principle, however, also other adhesive connections are possible, such as, e.g., holding together of annular platelet and electrode base by magnetic of electrostatic forces. When using a glue layer for forming the adhesive connection, various measures may be taken so as to keep the adhesive action at the side of the annular platelet facing away from the skin surface from becoming adversely apparent, on the one hand, when pressing the annular platelet to the skin surface, and nevertheless to achieve a good fixing of the base of the electrode on the annular platelet. Thus, an adhesive layer may be provided on the annular platelet, and pressing of the annular platelet can be accomplished with a tool that is largely inert to adhesive, or such an adhesive layer provided on the annular platelet may initially be covered by a protective film to be removed when the annular platelet has been pressed on; other variants provide for a respective adhesive layer on the side of the electrode base which is to face the annular platelet, or for special layers on the annular platelet and on the base of the electrode, which layers substantially merely adhere to each other, yet not to other bodies.

For a simple and exact handling of the stimulation electrode provided in the electrode system designed according to the invention, when applying the electrode system to the skin or piercing the latter therewith, it is advantageous if the disk-like base of the punctual stimulation electrode has an elevation at its side facing away from the needle or tip, which elevation is provided for a fitting insertion in a receiving aperture of a handling tool and for putting on an electric connecting terminal. In this manner, with a tool or relatively simple design, a good lateral guidance of the electrode can be attained when applying the latter to the skin surface or piercing the skin surface therewith, and thus also a good positioning at the site already defined by the annular platelet. Furthermore, by this elevation, a connection point for an electric connection terminal connecting a flexible line to the electrode can be created which does not influence the adhesive fit of the electrode on the annular platelet, such a connecting terminal e.g. being formed like a snap-fastener or in the manner of a C-spring. For as exact a fit as possible of the punctual stimulation electrode in a tool provided with a receiving aperture, it is, furthermore, suitable if it is provided for the elevation provided at the base of the punctual stimulation electrode to have a peripherally extending pronounced lateral rim, which rim is formed by straight lines extending in parallel to each other and approximately perpendicularly to the base, or which rim is formed to be undercut at least in partial regions thereof. The mentioned undercut design is particularly advantageous for an electric connection clip to be put thereon.

To attain an even greater protection of the electrode system from undesired, external influences also over extended periods of time, it is advantageous if a cover of the respective punctual stimulation electrode that is fixed to the skin surface by means of an adhesive annular platelet, is provided with a flexible adhesive tape disk adhering to the skin surface all around this electrode. In this instance, it is furthermore suitable—both, for the hold of the adhesive tape disk on the skin surface and also for the guiding of the line connected to the respective electrode, if the adhesive tape disk has an approximately radial incision for the passage of a line leading to the treatment current generator.

The handling tool designed according to the invention, which is provided for applying an electrode system, designed as mentioned before, to the skin surface, is characterized in that the tool has a hollow rod housing of a shape similar to a hand writing tool, which housing tapers to a tip at its front end and has an aperture at this front end through which an electrically conductive pin that is axially displaceably mounted in this housing can be pushed out by a part of its length and is also retractable through this aperture, an axial displacement mechanism controllable by at least one actuating element provided on the hollow rod housing being arranged in the hollow rod housing and coupled to this pin for pushing out and retracting the latter, that this pin is arranged in the tool without a direct electrically conductive connection to electrically conductive members provided on the housing surface, and is connected to at least one such electrically conductive member via a circuit arrangement arranged in the tool for measuring the electric resistance value, which circuit arrangement senses the value of the electric resistance of the respective current path which externally is applied between the electrically conductive pin and the said electrically conductive member, and that this circuit arrangement is connected to an optic and/or acoustic indicator. With this tool, the electrode system can be placed and fixed at the receptor regions to be stimulated in a very simple manner, and by an electric resistance measurement effected while moving over skin surface regions in question, appropriate sites can be determined and an annular platelet previously taken up by the handling tool can immediately be pressed to, or fixed at, respectively, such sites, whereupon the stimulation electrode is attached to or pierced into the thus labelled and prepared site, which likewise can be effected with this handling tool. The arrival at a receptor region in the course of moving over a skin surface area in question is signaled by an optic and/or acoustic indicator which advantageously is arranged in the housing of the handling tool in an appropriately recognizable manner.

For taking up the annular platelet with the handling tool and for applying the annular platelet to the skin surface it is advantageous if it is provided for the diameter of the electrically conductive, axially displaceably mounted pin at the aperture provided at the front end of the housing of the handling tool to correspond to the inner diameter of the annular platelet. In this manner, it is also made possible that the annular platelet will remain taken up on the pin without any additional measures and can be pressed to the skin surface at any time without difficulty, while locating receptor regions by moving over the skin surface with the electrically conductive pin. In this instance, the annular platelet can be pressed at the skin surface with the rim of the aperture through which the said conductive pin can be pushed out by a part of its length. For this purpose, the pin is pushed, or retracted, respectively, into the aperture, and this procedure can be effected by means of the controllable axial displacement mechanism with which this pin is coupled, or also automatically by the electrically conductive pin being coupled not only with the controllable axial displacement mechanism, but also being arranged to be resiliently displaceable in axial direction, so that this pin can be pushed back into the aperture surrounding it by appropriately pressing the handling tool to the skin surface against the spring force, the annular platelet sliding off the pin in axial direction and being pressed to the skin surface by the rim of the aperture surrounding the pin.

Advantageously, the aperture provided on the handling tool, from which the electrically conductive pin can be pushed out, is also designed to receive and retain electrodes which, as explained above, are provided with an elevation on the side of the disk-like base that faces away from the needle. A respective embodiment of the handling tool according to the invention is characterized in that the cross-section of the aperture provided on the front end of the housing of the handling tool is dimensioned for insertion of the elevation provided on the disk-like base of the punctual stimulation electrode. For receiving an electrode, in this instance, the electrically conductive pin at first must be retracted by the axial displacement mechanism to an extent that the elevation provided on the electrode can be introduced into the aperture. Application of the electrode to, and piercing of the skin surface therewith, can then be carried out by manually exerting pressure, with the electrode being pressed from the rim of the aperture, or with the aid of the axial displacement mechanism which presses the electrically conductive pin to the elevation of the electrode which at first is seated in the aperture.

In case of a resiliently displaceable arrangement of the electrically conductive pin which, as mentioned before, does not only serve as a tracing electrode for determining the position of receptor regions, but may also have various functions in the attachment of the annular platelet and the electrode, considering these functions and also for structural reasons it is advantageous if it is provided that for an axial resilience and for an axial displacement of the axially displaceably mounted pin, a first spring which is seated with its one end at a first fixed point in the tool and with its other end engages this pin, and furthermore, a serial arrangement formed of a second spring and an axial displacement mechanism is provided, one end of this serial arrangement being seated at a second fixed point in the tool, and the other end of this serial arrangement engaging said pin. In this respect, a suitable solution in terms of construction results if a first spring is provided which surrounds the axially displaceably mounted pin at its front portion and with its one end is seated on a fixed point in the vicinity of the aperture and with its other end engages the said pin, that on the rear portion of the pin a serial arrangement follows, formed of the axial displacement mechanism, a battery and a second spring, the second spring being seated on a second fixed point in the tool and also forming an electric connection to one pole of the battery.

As regards the axial displacement mechanism, a structurally simple, purely mechanical solution can be obtained by providing for the axial displacement mechanism to comprise two supporting bodies arranged in axial direction of the resiliently axially displaceably mounted pin following upon this pin and abutting each other in axial sequence and rotatable relative to each other and comprising surfaces that extend obliquely to the axial direction, oblique surfaces of the one supporting body contacting oblique surfaces of the other supporting body, and the axial total length of these two supporting bodies being changeable by relative rotation thereof, and one of these supporting bodies being non-rotationally arranged in the tool, while the other supporting body is rotatably arranged and connected to an actuating element arranged externally on the housing for rotation of this supporting body. As regards the axial displacement of the electrically conductive pin, which axial displacement, as mentioned above, is important for the function of this pin as a tracing electrode and also for the attachment of the annular platelet and the electrode, a structurally simple, gently working embodiment of the handling tool according to the invention can be obtained if it is provided that two axially acting springs engage the axially displaceably mounted pin, which springs are each supported with their ends facing away from the respective site of engagement on pin, on a fixed point in the housing that is fixed against an axial displacement, that the axial displacement mechanism is formed by a nose laterally projecting from the pin and a shifting body transversely movable to the axial direction of the pin, with at least one oblique surface being provided on the nose and/or on the shifting body, by which oblique surface the pin, at a movement of the shifting body transversely to the axial direction of the pin, in cooperation of nose and shifting body, is movable from a resting position in the direction of a pushing out of the aperture, and that the front end of the housing of the tool is formed by a cap arranged such that it can be axially offset relative to the remaining housing portion, wherein by this axial offsetting, the axial relative position of the aperture and the front end of the pin is changeable such that in one position of the cap, the pin which is in its resting position, projects a little from the aperture, and in another position of the cap the pin which is in its resting position is retracted a little relative to the outer rim of the aperture. In terms of a structurally simple solution for the axial offsetting of the cap which is easy to operate it is advantageous if it is provided for the axially offsettably arranged cap to be screwably arranged for said axial offsetting relative to the remaining housing portion. For a simple operation of the tool it is furthermore suitable if the shifting body is provided with a push button forming the actuating element.

A particularly gently working function of the axial displacement mechanism can be obtained in that a displacement gear driven by an electric motor or a solenoid means is provided as the axial displacement mechanism, which displacement gear can be controlled via easy-movable electric buttons or sensor fields. In such an embodiment, also the influence of forces which must be exerted on an actuating element of the axial displacement mechanism for controlling the latter can be largely eliminated, and if desired, also without a resilient arrangement of the electrically conductive pin, a sensitive movement of this pin corresponding to the respective requirements can be achieved, which is particularly advantageous when piercing the skin surface with the electrode.

The invention will now be explained in more detail by way of examples and with reference to the schematic drawings. In the drawings, FIG. 1 shows an inventively designed electrode system in section, and FIGS. 2, 3 and 4 show various stages when producing such an electrode system, in schematic sectional representations.

FIGS. 5 and 6 show variants, also in section, when piercing the skin with the stimulation electrode of such an electrode system, and FIGS. 7 and 8 show the provision of electric connections with such electrodes.

FIGS. 15 and 16 show a different embodiment of such an inventively designed handling tool in an elevational view, and in a partially exploded view.

Figure 9:
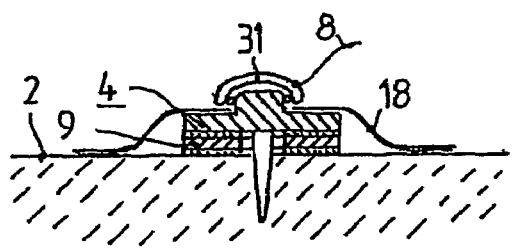
FIG. 9 shows a further embodiment of an inventively designed electrode system, in a schematic section.

The embodiment of an inventively designed electrode system 1 roughly schematically illustrated in section, which electrode system is provided for an electric punctual stimulation therapy, comprises a punctual stimulation electrode 4 which is to be arranged at receptor regions 3 located below the skin surface 2. The stimulation electrode 4 has a disk-like base 5 which in the middle thereof, at its side 6 to be turned towards the skin surface, is provided with a needle 7 with which the skin surface 2 is to be pierced. Via the stimulation electrode 4, a current is introduced into the receptor region 3 to be stimulated, and for this purpose, the stimulation electrode 4 is fed by a treatment current generator not further illustrated, via a flexible line 8. To fix the punctual stimulation electrode 4 on the skin surface 2, an annular plate or platelet 9 is provided which is to be arranged on the skin surface 2 before the skin is pierced by the electrode 4, which annular platelet 9 has an adhesive layer 11 at its side 10 which is to face the skin surface, for an adhesion on the skin surface, and furthermore, an adhesive connection 13 is provided between the other side 12 of annular platelet 9 and the needle-7-comprising side 6 of the disk-like base 5 of the stimulation electrode 4.

To form, or to apply, respectively, an electrode system designed as illustrated in FIG. 1, preferably first of all zones of the skin surface in which receptor regions may be located, are examined with respect to the presence of local deviations of the electric resistance value, whereupon an electrode system designed according to the invention is assembled or applied at locations found in this manner, at which receptor regions exist below the skin surface. For this purpose, as schematically illustrated in FIG. 2, a handling tool 21 may be used, which comprises an electrically conductive pin 25 which is arranged in a housing 22 of tool 21 so as to be shiftable in axial direction 26 and without a direct electrically conductive connection to the electrically designed parts of the housing 22 of the tool. In tool 21, also a circuit arrangement 27 is arranged which serves to measure the electric resistance value of a body which externally abuts between the electrically conductive pin 25 and an electrically conductive part 37 of housing 22. For this purpose, the circuit arrangement 27 is connected to pin 25, on the one hand, and to housing part 37, on the other hand. Then a therapist who handles tool 21 and who, in doing so, touches housing part 37, makes an electric connection to the skin surface 2 of a patient to be examined by mere manual contact or by using an auxiliary electrode 28, and pin 25, as indicated by double arrow 29, is led back and forth over the patient's skin surface 2 until a site of the skin surface is found at which a change of the value of the electric resistance is recognizable which is characteristic of the presence of a receptor region, with such a change of the electric resistance value being indicated by an indicator of the circuit arrangement 27 not further illustrated. If such a site of the skin surface 2, below which a receptor region 3 exists, has been found, an annular platelet 9 which previously has been slipped onto pin 25 and which has an adhesive layer 11 at its side 10 facing the skin surface 2, is pressed at the skin surface 2, such pressing, as shown in FIG. 3 possibly being performed by the rim of the aperture 24 of tool 21. In the course of this pressing-on procedure, the portion of pin 25 which previously has been shifted out of aperture 24, is pushed into the aperture, whereby pin 25 slides out of the aperture of annular platelet 9 and the annular platelet is fixed at the skin surface 2 by pressing on of tool 21 in the direction of arrow 30. When the pin 25 is mounted to be resilient in axial direction 26, the pushing back of pin 25 will occur automatically, or it may be caused by means of a suitable axial displacement mechanism to which pin 25 is coupled. As soon as the annular platelet 9 has been fixed at the skin surface 2, a punctual stimulation electrode which has a disk-like base 5, as shown in FIG. 4, is positioned for piercing the needle 7 of this electrode into a skin area located at the receptor region 3, according to the annular platelet 9 already fixed there, and pressed at the annular platelet, as indicated by arrow 30. In the instance illustrated in FIG. 4, an annular platelet 9 is used which is provided with an adhesive layer 20 at its side facing electrode 4, which adhesive layer will cause an adhesive connection (FIG. 1) between side 12 of annular platelet 9 facing electrode 4 and the needle-comprising side 6 of base 5 of electrode 4, as soon as the electrode 4 has been pressed at the annular platelet 9. As has already been mentioned above, also other variants are possible for making such an adhesive connection 13, e.g. in that an adhesive layer is provided on the side 6 of the base 5 of the electrode 4 which side 6 is to face the annular platelet 9. In order to obtain a good fit of the stimulation electrode in a handling tool, by which the former is secured against an unintentional lateral displacement, and also to provide for an easy to manipulate fastening site for the electric connection of a line to the respective electrode, advantageously an elevation 15 is provided at the base 5 of the electrode 4 at its side 14 that faces away from needle 7, which elevation is shaped for an appropriate insertion into a receiving aperture of a handling tool, as can be seen from FIGS. 5 to 8. Preferably, the dimensions will be chosen such that they will result in an easily adhering slide fit of such an elevation in a receiving aperture of the handling tool. Application of the stimulation electrode 4 may, as illustrated in FIG. 5, be effected by appropriately pressing the electrode with a tool 21 to the annular platelet that has previously been fixed at the skin surface, as illustrated in FIG. 6, by pushing out the stimulation electrode 4 provided with an elevation 15 seated in tool 21, by means of a pin 25 displaceable in the tool in a suitable manner, which pin 25 provides the pressure acting according to arrow 30 on the electrode, for pushing the latter out of tool 21 and for pressing it onto the annular platelet. To obtain the aforementioned sliding fit it is suitable if the elevation 15 has a peripherally extending pronounced lateral rim 16 formed by straight lines extending in parallel to each other, which straight lines extend approximately perpendicular to base 5. In case of a slight rounding, this will also result in a good fit for a snap-fastener-like connection 31 of a line 8 leading to the electrode (FIG. 7). If a simple spring clip 32 is provided for connecting such a line 8, it may be advantageous to provide the lateral rim 16 of the elevation 15 in partial regions thereof with undercut portions 17, as illustrated in FIG. 8.

Figure 10:
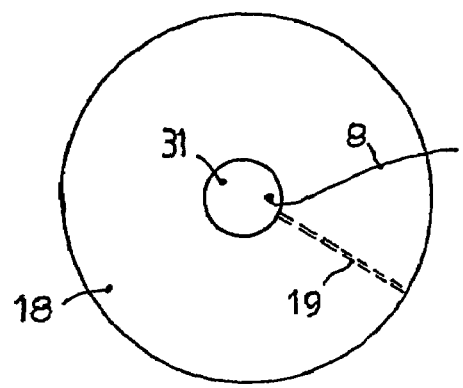
FIG. 10 shows this electrode system in a top view.

In the embodiment of an electrode system designed according to the invention and illustrated in FIGS. 9 and 10, a cover of the punctual stimulation electrode 4 which is fixed at the skin surface 2 by means of an adhesive annular platelet 9 is provided with an adhesive tape disk 18 which is designed to be flexible and adheres all around electrode 4 to the skin surface 2. This adhesive tape disk 18 has a central aperture through which the elevation 15 projects to the outside. Onto this elevation 15, a connection 31, a spring clip or a similar connection for a line 8 leading to electrode 4 is put. To facilitate the application of the adhesive tape, optionally an approximately radial incision 19 may be provided in the adhesive tape 18, as indicated in FIG. 10 in broken lines. The adhesive tape disk 18 very efficiently protects the electrode system from external interfering influences. In the variant illustrated in FIGS. 11 and 12, the adhesive tape disk 18 covers the electrode 4 and the connection 31 attached to this electrode, and the line 8 leading from electrode 4 to a treatment current generator not further illustrated is drawn through an approximately radial incision 19 provided in the adhesive tape disk 18, as can be seen from FIG. 12.

Figure 11:
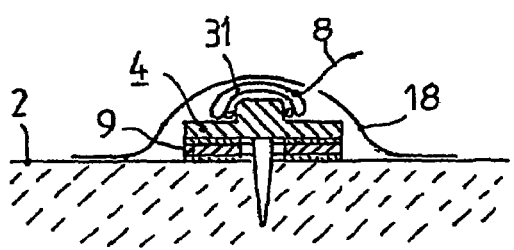
FIGS. 11 and 12 show a variant to the electrode system of FIGS. 9 and 10.
Figure 12:
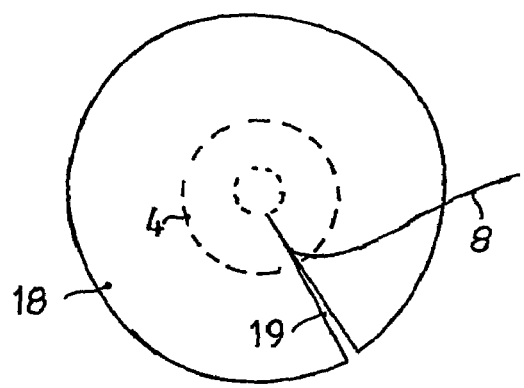
Figure 13:
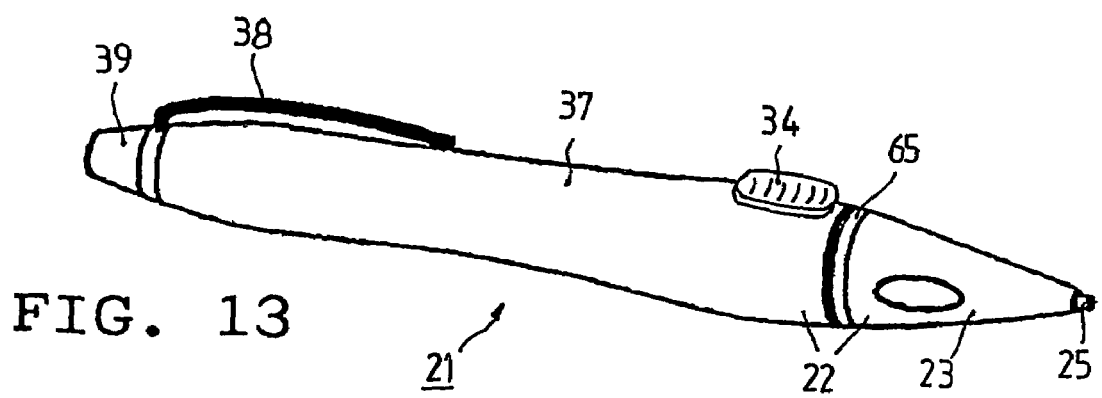
FIG. 13 shows an embodiment of an inventive handling tool for positioning, forming and applying an inventively designed electrode system in an elevational view.
Figure 14:
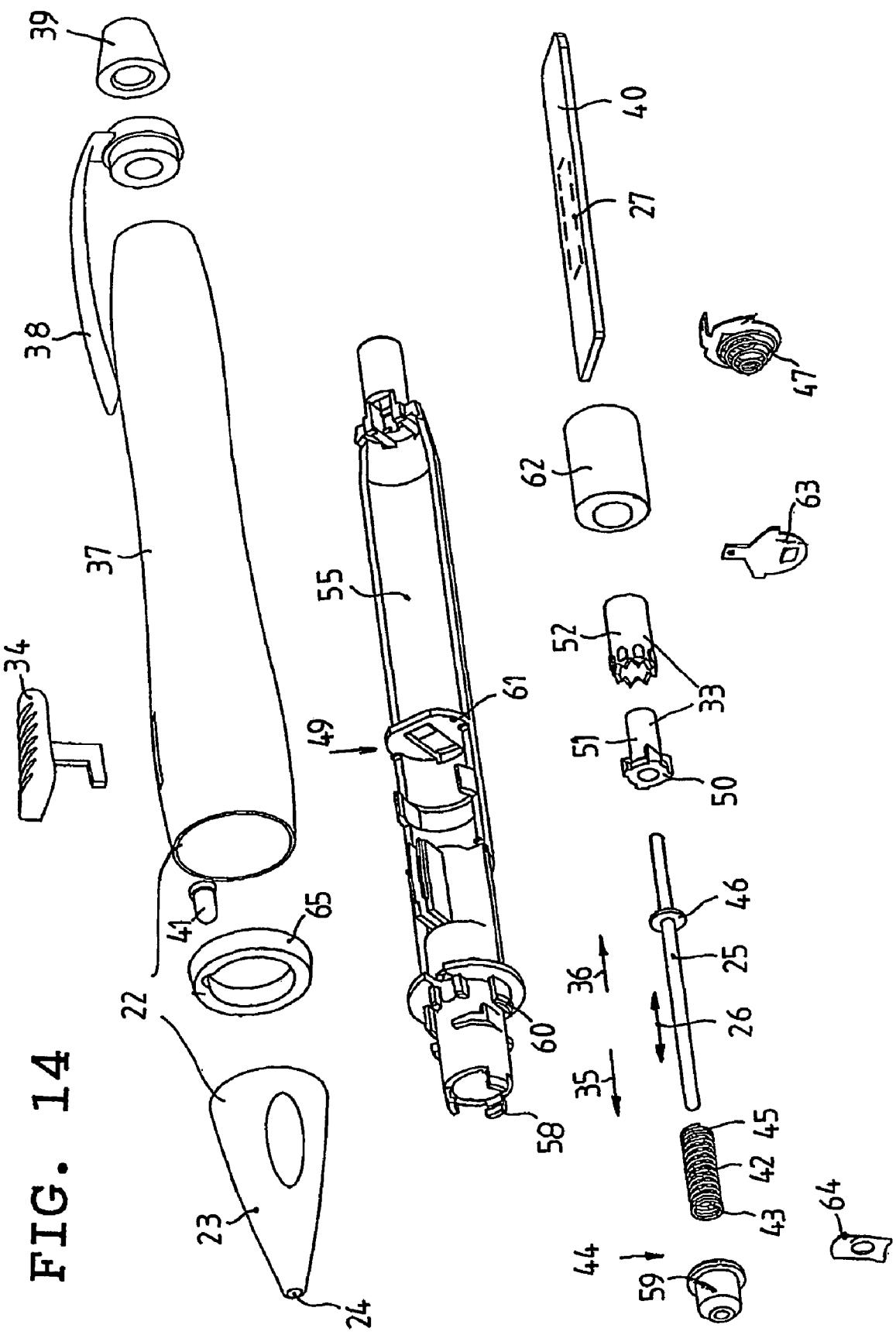
FIG. 14 shows this handling tool in an exploded representation.

The exemplary embodiment illustrated in FIGS. 13 and 14 of an inventive handling tool 21 has a hollow rod housing 22 similar in shape to a hand writing tool, which housing at its front end is formed by a cap 23 consisting of an insulating material, its remaining part being formed by a housing tube 37. The cap 23 forming the front has an aperture 24 through which an electrically conductive pin 25 that is axially displaceably mounted in housing 22 can be pushed out over a part of its longitudinal extension in the sense of arrow 35, and also retracted through this aperture 24 in the sense of arrow 36. Pin 25 is coupled to an axial displacement mechanism 33 which can be controlled by an actuating element 34 arranged externally on the hollow rod housing 22, so as to displace the pin 25 in its axial direction illustrated by the double arrow 26. In doing so, pin 25, as illustrated in FIG. 11, can be pushed out a little from aperture 24 by means of the axial displacement mechanism 33, and it can also be retracted into the interior of the tool by a distance of a few millimeters relative to the rim of aperture 24.

At the surface of the housing, at least one electrically conductive member is provided, such a member possibly being formed by the housing tube 37, a holding clip 38 or a closure cap 39, and wherein advantageously such electrically conductive members are also provided with a means allowing for the connection of an electrically connecting plug for connection of an auxiliary electrode. The electrically conductive pin 25 is connected with at least one such electrically conductive member 37, 38, 39 provided on the housing surface, via a circuit arrangement 27 designed to measure the electric resistance value. In other respects, pin 25 is electrically insulatedly arranged in tool 21 so that there is no direct electrically conductive connection to the electrically conductive members 37, 38, 39, and in this manner the value of the electric resistance of a body or current path externally abutting between the electrically conductive pin 25 and the electrically conductive members 37, 38, 39 can be sensed by the circuit arrangement 27. The circuit arrangement 27 is connected with an optic indicator 41, designed e.g. in the form of a light-emitting diode, this indicator possibly being designed for indicating the exceeding of a certain resistance value, or for a detailed indication of the respective resistance value present, by controlling the light intensity or by controlling the frequency of an intermittent light emission. Similarly, in addition to or instead of such an optic indicator, an acoustic indicator may be provided, wherein also in this instance detailed information on a prevailing resistance value or simply the fact that a certain limit value has been surpassed, can be indicated by an intensity variation or a sound frequency variation.

With the handling tool illustrated in FIGS. 13 and 14, a carrying member 55 is provided in housing 22 of this tool, in which carrying member a number of functional components of this tool are arranged, or housed, respectively. On the left-hand end in FIG. 12 (FIG. 13) of this carrying member, there is a latching seat 58 for a stop sleeve 59, and a latching seat 60 for putting on cap 23 which forms the front end of housing 22, aperture 24 being provided at the tip of this cap 23, through which aperture the electrically conductive pin 25 can be pushed out over part of its length. Pin 25 projects through an aperture provided in the stop sleeve 59. For an axial resilience and for an axial displacement of pin 25, a first spring 42 which abuts by its one end 43 on the stop sleeve 59 that forms a first fixed point 44, and by its other end 45 engages on a collar 46 of pin 25, and furthermore, a serial arrangement formed by a second spring 47 and the axial displacement mechanism 33 is provided. One end of this serial arrangement is seated on a second fixed point 49 in carrying member 55, which second fixed point is formed by a wall 61, and the other end 50 of this serial arrangement engages on collar 46 of pin 25. The axial displacement mechanism 33 comprises two supporting bodies 51, 52 arranged in axial direction 26 of pin 25 to follow upon this pin, and arranged in the carrying member 55 so as to contact each other in axial successive arrangement and so as to be rotatable relative to each other. The supporting bodies 51, 52 have surfaces extending obliquely to the axial direction 26, oblique surfaces of the one supporting body 51 contacting oblique surfaces of the other supporting body 52. These oblique surfaces are designed in the form of axially acting toothings, wherein in the course of a rotation of the two supporting bodies relative to each other, due to different heights of the teeth of one supporting body, these two supporting bodies will assume two different axial positions in alternating succession relative to each other, and in this manner the axial entire length of these two supporting bodies 51, 52 can be changed by a rotation relative to each other. One of these supporting bodies is non-rotationally arranged in the carrying member 55 of tool 21, while the other supporting body is rotationally arranged and connected to the axially movable actuating element 34 arranged externally on housing 22 for a rotation of this supporting body. The axial displacement mechanism 33 formed by the supporting bodies 51, 52 is slightly axially displaceable in the carrying member 55, and thus, pin 25 in its position in which it is somewhat pushed out of aperture 24 can be pushed back against the force of spring 47, which may be used for the automatic slipping off of an annular platelet slipped onto this pin when the latter is pressed to the skin surface. In the case illustrated, also a battery 62 is inserted in the serial arrangement that contains the axial displacement mechanism 33 and the second spring 47, said second spring also forming an electric connection to a pole of this battery 62. The other pole of battery 62 rests on a contact 63. The battery 62 serves to feed the circuit arrangement 27 formed on the circuit board 40, which circuit arrangement is connected by a line not further illustrated to a connection contact 64, on the one hand, which makes an electrical connection to pin 25, and is in connection with the electrically conductively designed housing tube 37, on the other hand. Furthermore, the light-emitting diode 41 provided as an optic indicator is connected to the circuit arrangement 27, which diode 41 is inserted in a transparent ring 65 that has the effect that the light of the diode 41 will be visible from all sides.

The diameter of pin 25 at its end that is capable of being pushed out of aperture 24 is chosen to be preferably equal to the inner diameter of the annular platelet to be applied by means of tool 21, so that these annular platelets will stay on this pin without additional measures after they have been slipped on, and can also be slipped off the pin easily. Furthermore, preferably, a slightly elastically yielding material will be chosen for producing the cap, and the diameter, or cross-section, respectively, of the aperture 24 will be chosen according to an easy sliding fit for insertion of elevations provided on the disk-like base of stimulation electrodes.

The aforementioned choice of the diameter of pin 25 and the diameter, or cross-section, respectively, of aperture 24 advantageously will also be made in the embodiment of a handling tool designed according to the invention and illustrated in FIGS. 15 and 16. In this embodiment, the electrically conductive pin 25 is axially displaceably arranged in a two-part electrically insulating bearing body 74, 75. The bearing body 74, 75 is fixedly seated in the electrically conductive housing tube 37. In the bearing body, also two springs 66, 67 acting in axial direction 26 of the pin 25 are arranged, which springs rest with their ends 68, 69 against one fixed body each, formed by bearing bodies 74, 75, and with their other ends engage on pin 25. Pin 25 is provided with noses 70 cooperating with oblique surfaces provided on a shifting body 71 which in turn is integrally formed with a push-button 73 that projects from the housing. When actuating the push-button 73, the pin is moved out of aperture 24 in the sense of a pushing out. The cap 72 forming the front end of the housing is axially offsettable, with the axially resiliently mounted pin 25 in the position illustrated in FIG. 15 projecting from the opening 24, and therefore can be used as a tracing electrode, and an annular platelet for application purposes can be slipped onto this pin. On account of the resilient bearing of pin 25, the latter can be pushed into the aperture 24, and thus the annular platelet can be applied to the skin surface. By an axial offsetting of the cap 72 in the direction of the push-out movement of pin 25, the forward end of the pin gets into the aperture, i.e. as far as to a few millimeters from the aperture rim, and then an electrode can be fixed on aperture 24 by insertion of an elevation provided on the electrode into the aperture. By actuating the push button 73, the pin 25 can be shifted towards the aperture 24, and thus the electrode can be pushed out of aperture 24 for application of the former. In the embodiment illustrated in FIGS. 15 and 16, the cap 72 has a bolt on its inner side which engages in an oblique groove 76 provided on the bearing body 74, and cap 72 thus carries out a helical movement axially offsetting this cap 72 during a rotation according to arrow 77. In this embodiment, pin 25 is connected with a mounting plate via spring 67 and a contact 78, which plate carries a circuit arrangement for measuring the electric resistance, and a battery. This circuit arrangement is also in connection with an indicator in the form of a light-emitting diode which is inserted in a lighting ring.

The invention claimed is:

1. A kit for an electrode system for an electric punctual stimulation therapy comprising:
   a) a punctual stimulation electrode comprising:
      i) a substantially disk shaped base;
      ii) a needle coupled to said substantially disk shaped base;
   b) a flexible line wherein said substantially disk shaped base is adapted to receive said flexible line for feeding power into said electrode;
   c) a handling tool having:
      i) a tracing pin; and
      ii) electrical circuitry configured to measure an electrical resistance value of a body in contact with said tracing pin; and
   d) an annular plate having a hole disposed in a center region of said plate, said plate being formed separate from said punctual stimulation electrode, and said annular plate having a first side for coupling to a patient's skin, said first side having a first adhesive layer, for adhesion of said annular plate to the skin, and a second side having an adhesive surface, forming a second adhesive layer for connection between said annular plate and said base, as well as, being spaced apart from said substantially disk shaped base before use of said electrode system, until said annular plate alone has been adhered to a patient's skin, wherein for precise positioning of said needle to a particular location on the skin first said annular plate is adapted to be slipped on said tracing pin being used for searching particular locations situated on the skin of a patient and having a diameter or cross section that corresponds to the dimensions of said hole of said annular plate and to be stripped off from said tracing pin at such a particular location found and indicated by said electrical circuitry and wherein said plate is applied using said first adhesive layer to said particular location on the skin wherein said handling tool is configured to apply said annular plate to a patient's skin; and then, using said hole of the annular plate for positioning the needle of said punctual stimulation electrode, said substantially disk shaped base is fixed to said second side of said annular plate via said second adhesive layer, resulting in said needle extending through said hole to puncture the patient's skin wherein coupling of said flexible line to said substantially disk shaped base is carried out after said needle punctures said patient's skin.

2. The electrode system as in claim 1, wherein said disk-like base has an elevation at its side facing away from the needle or the tip, wherein said elevation is provided for fitting said needle in a receiving aperture of a handling tool and for putting on an electric connecting terminal.

3. The electrode system according to claim 2, wherein said elevation has a peripherally extending pronounced lateral rim, which rim is formed by straight lines extending in parallel to each other and approximately perpendicularly to the base.

4. The electrode system according to claim 1, further comprising a cover for said punctual stimulation electrode that is fixed to the skin surface by means of said adhesive annular plate, and wherein said adhesive annular plate has a flexible adhesive tape disk adhering to the skin surface all around this electrode.

5. The electrode system according to claim 4, wherein said adhesive tape disk has an approximately radial incision for the passage of a line leading to the treatment current generator.

6. A kit for an electrode system for an electric punctual stimulation therapy comprising:
 a) a punctual stimulation electrode comprising:
  i) a substantially disk shaped base;
  ii) a needle coupled to said substantially disk shaped base;
 b) a flexible line wherein said substantially disk shaped base adapted to receive said flexible line for feeding power into the electrode;
 c) a handling tool having:
  i) a tracing pin;
  ii) electrical circuitry configured to measure an electrical resistance value of a body in contact with said tracing pin;
 d) an annular plate having a hole disposed in a center region of said plate, said plate being formed separate from said punctual stimulation electrode, and said annular plate having a first side for coupling to a patient's skin, said first side having a first adhesive layer, for adhesion of said annular plate to the skin, and a second side being spaced apart from said substantially disk shaped base before use of said electrode system, until said annular plate alone has been adhered to a patient's skin wherein said handling tool is configured to apply said annular plate to a patient's skin;
 e) an additional adhesive layer forming a second adhesive layer which is coupled to said substantially disk shaped base, said second adhesive layer for fixation of said base on said annular plate, wherein for precise positioning of said needle to a particular location on the skin, said annular plate is adapted to be slipped on said tracing pin being used for searching particular locations situated on the skin of a patient and wherein said tracing pin has a diameter or cross section that corresponds to the dimensions of said hole of said annular plate and wherein said annular plate is stripped off from said tracing pin at such a particular location found and indicated by said electrical circuitry and wherein said plate is applied using said first adhesive layer to said particular location on the skin, and then using said hole of the annular plate for positioning the needle of said punctual stimulation electrode, said substantially disk shaped base is fixed to said second side of said annular plate via said second adhesive layer, resulting in said needle extending through said hole in said annular plate to puncture the patient's skin wherein said coupling of flexible line to said substantially disk shaped base is carried out after said needle punctures said patient's skin.

7. The electrode system as in claim 6, wherein said disk-like base has an elevation at its side facing away from said needle, wherein said elevation is provided for fitting said punctual stimulation electrode in a receiving aperture of a handling tool and for putting on an electric connecting terminal.

8. The electrode system according to claim 7, wherein said elevation has a peripherally extending pronounced lateral rim, wherein said rim is formed by straight lines extending in parallel to each other and approximately perpendicularly to the base.

9. The electrode system according to claim 6, further comprising a cover for said punctual stimulation electrode that is fixed to the skin surface by means of said adhesive annular plate, and wherein said cover has a flexible adhesive tape disk adhering to the skin surface all around this electrode.

10. The electrode system according to claim 9 wherein said adhesive tape disk has an approximately radial incision for the passage of a line leading to the treatment current generator.

11. A kit for an electrode system for an electric punctual stimulation therapy comprising:
 a) a punctual stimulation electrode comprising:
  i) a substantially disk shaped base;
  ii) a needle coupled to said substantially disk shaped base;
 b) a handling tool comprising:
  i) a tracing pin, and
  ii) electrical circuitry configured to measure an electrical resistance value of a body in contact with said tracing pin;
 c) a flexible line wherein said substantially disk shaped base is adapted to receive said flexible line;
 d) an annular plate having a hole disposed in a center region of said plate, said annular plate being formed separate from said punctual stimulation electrode and separate from said handling tool, said plate having a first side having an adhesive and a second side having an adhesive, said first side for adhering said plate to a patient's skin, said second side for coupling said plate to said punctual stimulation electrode;

wherein said hole of said annular plate is adapted to accept the needle of said punctual stimulation electrode and to accept said tracing pin of said handling tool, and wherein said electrical circuitry is adapted to indicate where said annular plate should be placed by slipping off from said tracing pin.

12. The kit as in claim 11, wherein said handling tool comprises a housing, comprising an aperture configured to receive said tracing pin, and wherein said tracing pin is slidably mounted in said housing and configured to be extended outside of said housing or retracted inside of said housing.

13. The kit as in claim 12, wherein said housing of said handling tool has surrounding said aperture, a surface that is smaller than the diameter of said annular plate.

14. A kit for an electrode system for an electric punctual stimulation therapy comprising:
 a) a punctual stimulation electrode comprising:
  i) a substantially disk shaped base;
  ii) a needle coupled to said substantially disk shaped base;
 b) a handling tool comprising:
  i) a tracing pin, and
  ii) electrical circuitry configured to measure an electrical resistance value of a body in contact with said tracing pin;
 c) a flexible line wherein said substantially disk shaped base is adapted to receive said flexible line;
 d) an annular plate having a hole disposed in a center region of said plate, said annular plate being formed separate from said punctual stimulation electrode and separate from said handling tool, said plate having a first side having an adhesive for adhering said plate to a patient's skin, coupling said plate to said punctual stimulation electrode;
 e) an additional adhesive layer for fixation of said base of said punctual stimulation electrode on said annular plate;

wherein said hole of said annular plate is adapted to accept the needle of said punctual stimulation electrode and to accept said tracing pin of said handling tool, and wherein said electrical circuitry is adapted to indicate where said annular plate should be placed by slipping off from said tracing pin.

15. The kit as in claim 14, wherein said handling tool comprises a housing, comprising an aperture configured to receive said tracing pin, and wherein said tracing pin is slidably mounted in said housing and configured to be extended outside of said housing or retracted inside of said housing.

16. The kit as in claim 15, wherein said housing of said handling tool has surrounding said aperture a surface that is smaller than the diameter of said annular plate.

* * * * *

UNITED STATES PATENT AND TRADEMARK OFFICE
CERTIFICATE OF CORRECTION

| | | |
|---|---|---|
| PATENT NO. | : 7,660,637 B2 | Page 1 of 1 |
| APPLICATION NO. | : 10/432336 | |
| DATED | : February 19, 2010 | |
| INVENTOR(S) | : Szeles | |

It is certified that error appears in the above-identified patent and that said Letters Patent is hereby corrected as shown below:

In particular, on the Title page, Item [73], please change the country of the Assignee from "(AU)" to correctly read:   -- (AT) --.

Signed and Sealed this

Fifteenth Day of June, 2010

David J. Kappos
*Director of the United States Patent and Trademark Office*